United States Patent [19]

Bernstein et al.

[11] 4,131,684

[45] Dec. 26, 1978

[54] COMPLEMENT INHIBITORS

[75] Inventors: Seymour Bernstein; Milton D. Heller, both of New City, N.Y.

[73] Assignee: American Cyanamid Company, Stamford, Conn.

[21] Appl. No.: 833,319

[22] Filed: Sep. 14, 1977

Related U.S. Application Data

[62] Division of Ser. No. 684,601, May 10, 1976, abandoned.

[51] Int. Cl.$^2$ ............................................. A61K 31/185
[52] U.S. Cl. .................................................... 424/315
[58] Field of Search ......................................... 424/315

[56] References Cited

U.S. PATENT DOCUMENTS

| | | | |
|---|---|---|---|
| 4,027,038 | 5/1977 | Bernstein et al. | 424/315 |
| 4,046,805 | 9/1977 | Bernstein | 424/315 |
| 4,051,176 | 9/1977 | Bernstein et al. | 424/315 |
| 4,087,548 | 5/1978 | Lenhard et al. | 424/315 |

*Primary Examiner*—Donald B. Moyer
*Attorney, Agent, or Firm*—Jack W. Richards

[57] ABSTRACT

Certain C-substituted-hydroxynaphthalenesulfonic acids, salts and ureides useful as complement inhibitors.

2 Claims, No Drawings

COMPLEMENT INHIBITORS

This is a division of application Ser. No. 684,601, filed May 10, 1976 now abandoned.

BACKGROUND OF THE INVENTION

The present invention resides in the concept of certain C-substituted-hydroxynaphthalenesulfonic acids, salts, and ureides, for example, (C4-substituted) 5-hydroxy-1-naphthalenesulfonic acids, which are new compounds useful as complement inhibitors, and in certain other known compounds, namely certain (C4-substituted) 5-hydroxy-1-naphthalenesulfonic acids and 5-hydroxy-1-naphthalenesulfonic acid ureides as well as (C6-substituted) 4-hydroxy-2-naphthalenesulfonic acids and 4-hydroxy-2-naphthalenesulfonic acid ureides, useful as inhibitors of the complement system of warm-blooded animals.

The term "complement" refers to a complex group of proteins in body fluids that, working together with antibodies or other factors, play an important role as mediators of immune, allergic, immunochemical and/or immunopathological reactions. The reactions in which complement participates takes place in blood serum or in other body fluids, and hence are considered to be humoral reactions.

With regard to human blood, there are at present more than 11 proteins in the complement system. These complement proteins are designated by the letter C and by number: C1, C2, C3 and so on up to C9. The complement protein C1 is actually an assembly of subunits designated C1q, C1r and C1s. The numbers assigned to the complement proteins reflect the sequence in which they become active, with the exception of complement protein C4, which reacts after C1 and before C2. The numerical assignments for the proteins in the complement system were made before the reaction sequence was fully understood. A more detailed discussion of the complement system and its role in body processes can be found in, for example, *Bull. World Health Org.*, 39, 935-938 (1968); *Scientific American* 229, (No. 5), 54-66 (1973); *Medical World News*, Oct. 11, 1974, pp. 53-58; 64-66; *Harvey Lectures*, 66, 75-104 (1972); *The New England Journal of Medicine*, 287 489-495; 545-549; 642-646 (1972); *The Johns Hopkins Med. J.*, 128, 57-74 (1971); and *Federation Proceedings*, 32, 134-137 (1973).

The complement system can be considered to consist of three sub-systems: (1) a recognition unit (C1q) which enables it to combine with antibody molecules that have detected a foreign invader; (2) an activation unit (C1r, C1s, C2, C4, C3), which prepares a site on the neighboring membrane; and (3) an attack unit (C5, C6, C7, C8 and C9) which creates a "hole" in the membrane. The membrane attack unit is non-specific it destroys invaders only because it is generated in their neighborhood. In order to minimize damage to the host's own cells, its activity must be limited in time. This limitation is accomplished partly by the spontaneous decay of activated complement and partly by interference by inhibitors and destructive enzymes. The control of complement, however, is not perfect, and there are times when damage is done to the host's cells. Immunity is therefore a double-edged sword.

Activation of the complement system also accelerates blood clotting. This action comes about by way of the complement-mediated release of a clotting factor from platelets. The biologically active complement fragments and complexes can become involved in reactions that damage the host's cells, and these pathogenic reactions can result in the development of immune-complex diseases. For example, in some forms of nephritis complement damages the basal membrane of the kidney, resulting in the escape of protein from the blood into the urine. The disease disseminated lupus erythematosus belongs in this category; its symptoms include nephritis, visceral lesions and skin eruptions. The treatment of diptheria or tetanus with the injection of large amounts of antitoxin sometimes results in serum sickness, an immune-complex disease. Rheumatoid arthritis also involves immune complexes. Like disseminated lupus erythematosus, it is an autoimmune disease, in which the disease symptoms are caused by pathological effects of the immune system in the host's tissues. In summary, the complement system has been shown to be involved with inflammation, coagulation, fibrinolysis, antibody-antigen reactions and other metabolic processes.

In the presence of antibody-antigen complexes the complement proteins are involved in a series of reactions which may lead to irreversible membrane damage if they occur in the vicinity of biological membranes. Thus, while complement constitutes a part of the body's defense mechanism against infection, it also results in inflammation and tissue damage in the immunopathological process. The nature of certain of the complement proteins, suggestions regarding the mode of complement binding to biological membranes and the manner in which complement effects membrane damage are discussed in *Annual Review in Biochemistry*, 38, 389 (1969).

A variety of substances have been disclosed as inhibiting the complement system, i.e., as complement inhibitors. For example, the compounds 3,3'-ureylenebis[6-(2-amino-8-hydroxy-6-sulfo-1-naphthylazo)]benzenesulfonic acid tetrasodium salt (chlorazol fast pink), heparin and a sulphated dextran have been reported to have an anticomplementary effect, *British Journal of Experimental Pathology*, 33, 327-339 (1952). The compound 8,8'-ureylenebis[m-phenylenecarbonylimino(4-methyl-m-phenylene)carbonylimino] di-1,3,5-naphthalenetrisulfonic acid, hexasodium salt (Suramin Sodium) is described as a competitive inhibitor of the complement system, *Clin. Exp. Immunol.*, 10, 127-138 (1972). German Pat. No. 2,254,893 or South African Pat. No. 727,923 discloses certain 1-(diphenylmethyl)-4-(3-phenylallyl)piperazines useful as complement inhibitors and U.S. Pat. No. 3,897,434 certain pyrazolo[1,5-c]quinazolin-5 (6H)-ones as complement inhibitors. The compound, m-[m-(p-nitrophenylureido)phenoxypropoxyl]benzamidine is also a complement inhibitor, *Immunology*, 26, 819 (1974). Other chemical compounds having complement inhibiting activity are disclosed in, for example, *Journal of Medicinal Chemistry*, 12, 415-419; 902-905; 1049-1052; 1053-1056 (1969); *Canadian Journal of Biochemistry*, 47, 547-552 (1969); *The Journal of Immunology*, 93, 629-640 (1964); *The Journal of Immunology*, 104, 279-288 (1970); *The Journal of Immunology*, 106, 241-245 (1971); and *The Journal of Immunology*, 111, 1061-1066 (1973).

It has been reported that the known complement inhibitors epsilon-aminocaproic acid, Suramin Sodium and tranexamic acid have been used with success in the treatment of hereditary angioneurotic edema, a disease state resulting from an inherited deficiency or lack of function of the serum inhibitor of the activated first component of complement (C1 inhibitor), *The New*

England Journal of Medicine, 286, 808–812 (1972); Allergol, Et. Immunopath., II, 163–168 (1974); and J. Allergy Clin. Immunol., 53, No. 5, 298–302 (1974).

SUMMARY OF THE INVENTION

It has now been discovered that certain (C4-substituted) 5-hydroxy-1-naphthalenesulfonic acids and 5-hydroxy-1-naphthalenesulfonic acid ureides, as well as certain (C6-substituted) 4-hydroxy-2-naphthalenesulfonic acids and 4-hydroxy-2-naphthalenesulfonic acid ureides interact with the complement reaction sequence, thereby inhibiting complement activity in body fluids.

This invention is concerned with new C-substituted-hydroxynaphthalenesulfonic compounds which may be represented by formula (I):

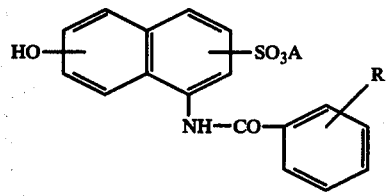

wherein R is selected from the group comprising

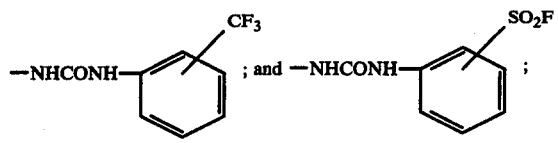

and A is hydrogen, alkali metal or alkaline earth, with the proviso that each A is identical in the same compound. Preferably, A is sodium or potassium.

This invention is particularly concerned with new C4-substituted 5-hydroxy-1-naphthalenesulfonic compounds which may be represented by formula (II):

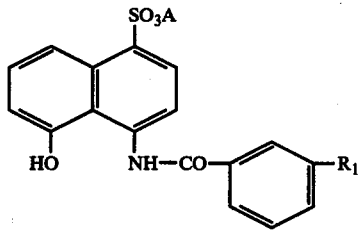

wherein $R_1$ is selected from the group comprising

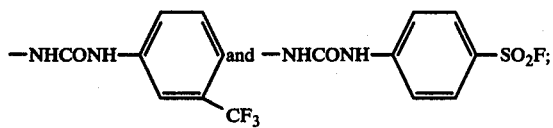

and A is hydrogen, alkali metal or alkaline earth with the proviso that each A is identical in the same compound.

Of particular interest as new compounds are those which may be represented by formula (III):

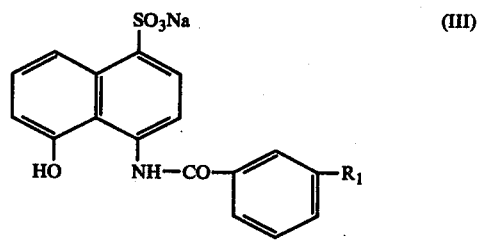

wherein $R_1$ is selected from the group comprising

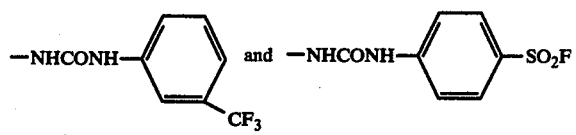

This invention is concerned with a new use for the new compounds of this invention represented hereinabove by formulae (I), (II) and (III), as well as with the new use of known compounds, said compounds collectively being represented by formula (IV):

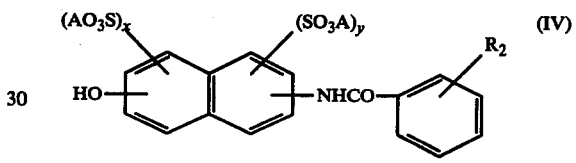

wherein $R_2$ is selected from the group comprising

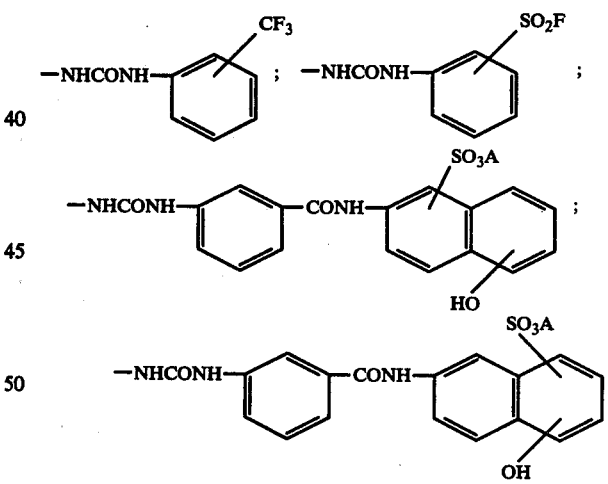

and —$NH_2$; x and y equal zero or 1; and A is hydrogen, alkali metal or alkaline earth, with the proviso that each A is identical in the same compound and both x and y are not one in the same compound and when x is 1, $R_2$ can only be —$NH_2$ and

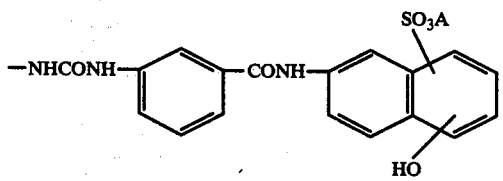

This invention is particularly concerned with a new use for the new compounds represented by formula (III) hereinabove, and with a new use for known compounds represented by formula (V):

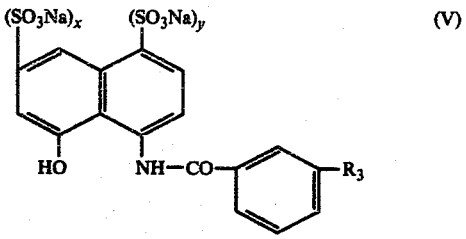

wherein $R_3$ is selected from the group comprising —$NH_2$;

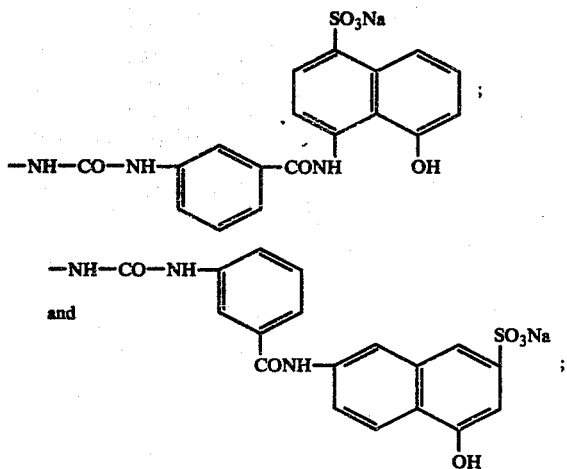

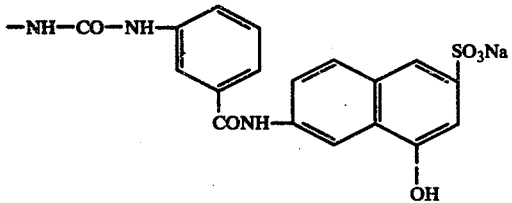

x and y equal 0 or 1, with the proviso that both x and y are not 1 in the same compound and when x is 1, $R_3$ can only be —$NH_2$ and The following references disclose known compounds of this invention: *J. Chem. Soc.*, 3068 (1927) *J. Chem. Soc.*, 3739 (1956) *Biol. Chem. J.*, 42, 109 (1948) *Bio. Chem. J.*, 47, 158 (1950) *Ann. Inst. Pasteur*, 38, 81 (1924).

The new use of this invention is a method of inhibiting the complement system in a body fluid which comprises subjecting said body fluid to the action of an effective complement inhibiting amount of a compound encompassed within formula (I)–(V) hereinabove. The new use of this invention is also concerned with a method of inhibiting the complement system in a warm-blooded animal which comprises internally administering to said animal an effective complement inhibiting amount of a compound encompassed within a formula (I)–(V) hereinabove.

This invention is specifically concerned with the following new compounds: 5-hydroxy-4-m-[3-(α,α,α-trifluoro-m-tolyl)ureido]benzamido-1-naphthalenesulfonic acid sodium salt; and 4-m-3-[p-(Fluorosulfonyl)-phenyl]ureido benzamido-5-hydroxy-1-naphthalenesulfonic acid sodium salt; and with a method of treatment involving the following known compounds; 5-hydroxy-4-m-nitrobenzamido-1-naphthalenesulfonic acid sodium salt; 4-(m-aminobenzamido)-5-hydroxy-1-naphthalenesulfonic a acid sodium salt; 4,4'-[ureylenebis(m-phenylenecarbonylimino)] [5-hydroxy-1-naphthalenesulfinic acid] disodium salt; 6-(m-aminobenzamido)-4-hydroxy-2-naphthalenesulfonic acid sodium salt; and 6,6'-[ureylenebis(m-phenylenecarbonylimino)] bis[4-hydroxy-2-naphthalenesulfonic acid] disodium salt.

The compounds of the present invention can be prepared by acylation of the respective naphthylaminesulfonic acid with m-nitrobenzoyl chloride followed by catalytic reduction and subsequent condensation of the respective amine with the appropriate substituted phenylisocyanate; or by phosgenation of the respective amine. The free acids can be prepared by manners known in the art. A more explicit outline of the reactions follows:

Schotten-Baumann Acylation

To a solution of the sodium salt of a naphthylaminesulfonic acid in an appropriate amount of water and 1N sodium hydroxide is added m-nitrobenzoyl chloride. The mixture is shaken until no longer basic to test paper. Three additional equal portions of 1N sodium hydroxide are added, shaking between each addition until the solution is no longer basic. After the last portion of base is added, the reaction mixture is shaken for at least 30 minutes and then the still basic solution is acidified to Congo Red with concentrated hydrochloric acid. The reaction mixture is then copiously extracted with ether to remove the m-nitrobenzoic acid side product (by vacuum siphoning of the ethereal layer). The aqueous phase is then filtered to remove a small amount of the anhydride of m-nitrobenzoic acid and the filtrate is concentrated in vacuo at 50°–60° C. until a solid is precipitated. After cooling to ambient temperature, the product is filtered and is washed with saturated saline solution, 50% ethyl alcohol, absolute ethyl alcohol and ether.

Catalytic Reduction

Treatment of a solution of the appropriate amount of the desired m-nitrobenzamide of naphthalenesulfonic acid in 160–200 ml of water with 1.0–3.7 g of 10% palladium on carbon in a Parr apparatus under an initial hydrogen pressure of 42 pounds per square inch gives a theoretical uptake of hydrogen in 1¾ hours. The reaction mixture is filtered through diatomaceous earth and the catalyst is washed with water. The filtrate is concentrated under reduced pressure at 50°–60° C. to low volume and is then diluted with a large volume of absolute ethanol. The precipitated product is collected and is washed with absolute ethyl alcohol.

Phosgenation

Phosgene is bubbled through a mechanically stirred solution of the desired aminobenzamide of naphthalenesulfonic acid in the appropriate amount of water containing a theoretical quantity of sodium carbonate until the reaction mixture becomes acidic to Congo Red. An additional quantity of carbonate is cautiously added and the process is repeated until the reaction mixture is again acidic. It is then neutralized with bicarbonate and is concentrated in vacuo at 50°–60° C. On cooling to room temperature a solid is formed which is filtered and is washed with 80% ethyl alcohol, absolute ethyl alcohol and ether.

Acylation With Isocyanates

A solution of the appropriate amount of the desired m-aminobenzamide of naphthalenesulfonic acid sodium salt in water is treated with a theoretical portion of the required isocyanate and is stirred vigorously for 6 hours at room temperature. The reaction mixture is diluted with additional water, is heated to approximately 95° C. for 30 minutes and is filtered through diatomaceous earth and is washed with hot water. The filtrate is treated with sodium chloride while heating on the steam bath and is allowed to stand at room temperature overnight (lower temperature is required in some cases). The precipitate is collected and is boiled with absolute ethyl alcohol then is allowed to stand at room temperature for several days. The product is then filtered and washed with absolute ethyl alcohol and ether.

This invention is concerned with a method of inhibiting the complement system in a body fluid, such as blood serum, which comprises subjecting body fluid complement to the action of an effective complement inhibiting amount of a compound encompassed within the formulae hereinabove. The method of used aspect of this invention is also concerned with a method of inhibiting the complement system in a warm-blooded animal which comprises internally administering to said animal an effective complement inhibiting amount of a compound encompassed within the formulae hereinabove. Body fluid can include blood, plasma, serum, synovial fluid, cerebrospinal fluid, or pathological accumulations of fluid as pleural effusion, etc.

The compounds of the present invention find utility as complement inhibitors in body fluids and as such may be used to ameliorate or prevent those pathological reactions requiring the function of complement and in the therapeutic treatment of warm-blooded animals having immunologic diseases such as rheumatoid arthritis, systemic lupus erythematosus, certain kinds of glomerulonephritis, certain kinds of auto-allergic hemolytic anemia, certain kinds of platelet disorders and certain kinds of vasculitis. The compounds herein may also be used in the therapeutic treamtent of warm-blooded animals having non-immunologic diseases such as paroxysmal nocturnal hemoglobinuria, hereditary angioneurotic edema (treated with Suramin, etc.) and inflammatory states induced by the action of bacterial or lysosomal enzymes on the appropriate complement components as for example, inflammation following coronary occlusion. They may also be useful in the treatment of transplant rejection and as blood culture or transport mediums.

DETAILED DESCRIPTION OF THE INVENTION

The following examples will serve to illustrate the invention in more detail.

Example 1

5-Hydroxy-4-m-nitrobenzamido-1-naphthalenesulfonic acid sodium salt

A 43 g portion of recrystallized 8-amino-1-naphthol-5-sulfonic acid is suspended in 80 ml of water and 180 ml of 1N sodium hydroxide is added, then 66.6 g of m-nitrobenzoyl chloride is added all at once, washing in with a small amount of ether. The mixture is shaken for 5 minutes and another 180 ml of 1N sodium hydroxide is added with shaking for ½ hour. The latter addition of sodium hydroxide and shaking is repeated two more times. The resulting solution is filtered and the filtrate is made acid to Congo Red with hydrochloric acid, a precipitate forms which is collected by filtration. The solid is stirred with about 500 ml of ether and is filtered. This operation is repeated. The ethereal layer is then removed by vacuum siphoning and the solid is then dissolved in about 350 ml of hot water which is allowed to cool to give the product as a green solid which is collected by filtration. The product is then washed with saturated saline solution, 50% ethyl alcohol, absolute ethyl alcohol and ether.

Example 2

4-(m-Aminobenzamido)-5-hydroxy-1-naphthalenesulfonic acid sodium salt

A mixture of 14.91 g of 5-hydroxy-4-m-nitrobenzamido-1-naphthalenesulfonic acid, 160 ml of distilled water and 1.0 g of 10% palladium on charcoal is hydrogenated in a Parr shaker for 2 hours at room temperature, during which time 10 pounds of hydrogen is absorbed. The mixture is heated to dissolve some precipitated product and is filtered hot to remove the catalyst. The filtrate is then evaporated to dryness in vacuo at about 60° C. A small amount of water is added to the residue which is then filtered and air dried to give the final product.

Example 3

5-Hydroxy-4-m-[3-(α,α,α-trifluoro-m-tolyl)ureido]-benzamido-1-naphthalenesulfonic acid sodium salt A mixture of 3.0 g of 4-(m-aminobenzamido)-5-hydroxy-1-naphthalenesulfonic acid sodium salt (prepared as in Example 2), 40 ml of water and 3.0 ml of m-trifluoromethylphenyl isocyanate is stirred for 6 hours, then is filtered hot through diatomaceous earth. The filtrate is treated with 5 g of sodium chloride while hot, then is allowed to stand overnight at room temperature. The precipitate formed is collected by filtration and dried at 120° C. to give the product of the example.

EXAMPLE 4

4-m-3-[p-(Fluorosulfonyl)phenyl]ureido benzamido-5-hydroxy-1-naphthalenesulfonic acid sodium salt A mixture of 18.0 g of sulfanilyl fluoride, 20 g of p-nitrophenyl chloroformate, and 95 ml of redistilled benzene is stirred and refluxed for a 5 hour period. The resulting mixture is then cooled and filtered and the precipitate is washed with cold benzene. The product is then recrystallized from methylene chloride to give 17.17 g of p-(fluorosulfonyl)carbanilic acid p-nitrophenyl ester.

A mixture of 4.0 g of 5-hydroxy-4-m-aminobenzamido-1-naphthalenesulfonic acid sodium salt in 40 ml of dimethylformamide (dried over 4A molecular sieve) and 16 g of 3A molecular sieve (Linde type 1/16″) is stirred for 1 hour at ambient temperature then 3.12 g of p-(fluorosulfonyl)carbanilic acid p-nitrophenyl ester in 16 ml of dimethylformamide is added and stirring is continued for an additional 18 hours at room temperature. The resulting mixture is then filtered through diatomaceous earth and the filter is washed with dimethylformamide. The combined filtrate and washings are diluted with 1 liter of diethyl ether, this solution is allowed to stand for 72 hours at 5° C. The mixture is then filtered and the final product of the example is collected.

Example 5

4,4'-[Ureylenebis(m-phenylenecarbonylimino)bis[5-hydroxy-1-naphthalenesulfonic acid] disodium salt To a stirred solution of 18 g of 4-(m-aminobenzamido)-5-hydroxy-1-naphthalenesulfonic acid sodium salt and 74 g of sodium carbonate in 400 ml of water is bubbled in phosgene at ambient temperature for 6 hours, until blue to Congo Red indicator. An additional 77 g of sodium carbonate is added and additional phosgene is added until the solution is acid to Congo Red again. Then sodium bicarbonate is added until the solution is just slightly alkaline. The solution is concentrated to about 150 ml and 300 ml of 95% ethyl alcohol is added. The resulting mixture is cooled at $-5°$ C. overnight then is filtered. The solid collected is redissolved in water which is then concentrated. Upon addition of anhydrous ethyl alcohol the product is collected as an amorphous green precipitate.

Example 6

6-(m-Aminobenzamido)-4-hydroxy-2-naphthalenesulfonic acid sodium salt

A 7.04 g portion of 4-(m-aminobenzamido)-5-hydroxy-1-naphthalenesulfonic acid sodium salt is heated in 200 ml of distilled water until solution is achieved then is allowed to cool until solid reappears. A 3.7 g portion of 10% palladium on charcoal is added and the mixture is hydrogenated in a Parr shaker for 1½ hours at room temperature during which time 4 pounds of hydrogen is absorbed. The mixture is heated to dissolve some precipitated product and is filtered hot to remove the catalyst. The filtrate is then concentrated in vacuo to about 20 ml and 200 ml of ethyl alcohol is added. The precipitate formed is collected by filtration and is air dried to give the product of the example.

Example 7

6,6'-[Ureylenebis(m-phenylenecarbonylimino)]bis[4-hydroxy-2-naphthalenesulfonic acid] disodium salt To a stirred solution of 12.21 g of 6-(m-aminobenzamido)-4-hydroxy-2-naphthalenesulfonic acid sodium salt and 50 g of sodium carbonate in 380 ml of water is bubbled in phosgene at room temperature for a period of 6 hours. The resulting solution which is red to Congo Red test paper is filtered slowly to remove a small amount of solid. A 1000 ml portion of methyl alcohol is added to the filtrate and the precipitate formed is collected to give the crude product which is contaminated with sodium chloride. The material is dissolved in water and is acidified with 12N hydrochloric acid. The precipitate formed is collected and is purified by selective precipitation from aqueous solution with ethyl alcohol then is collected and is washed with absolute ethyl alcohol followed by ether to give the desired product in low yield.

Example 8

| Preparation of Compressed Tablet | |
|---|---|
| Ingredient | mg/Tablet |
| Active Compound | .5–500 |
| Dibasic Calcium Phosphate NF | qs |
| Starch USP | 40 |
| Modified Starch | 10 |
| Magnesium Stearate USP | 1–5 |

Example 9

| Preparation of Compressed Tablet-Sustained Action | |
|---|---|
| Ingredient | mg/Tablet |
| Active Compound as Aluminum Lake*, Micronized | 0.5–500 (as acid equivalent) |
| Dibasic Calcium Phosphate NF | qs |
| Alginic Acid | 20 |
| Starch USP | 35 |
| Magnesium Stearate USP | 1–10 |

*Complement inhibitor plus aluminum sulfate yields aluminum complement inhibitor. Complement inhibitor content in aluminum lake ranges from 5–30%

Example 10

| Preparation of Hard Shell Capsule | |
|---|---|
| Ingredient | mg/Capsule |
| Active Compound | 0.5–500 |
| Lactose, Spray Dried | qs |
| Magnesium Stearate | 1–10 |

Example 11

| Preparation of Oral Liquid (Syrup) | |
|---|---|
| Ingredient | % W/V |
| Active Compound | 0.05–5 |
| Liquid Sugar | 75.0 |
| Methyl Paraben USP | 0.18 |
| Propyl Pavaben USP | 0.02 |
| Flavoring Agent | qs |
| Purified Water qs ad | 100.0 |

Example 12

| Preparation of Oral Liquid (Elixir) | |
|---|---|
| Ingredient | % w/v |
| Active Compound | 0.05–5 |
| Alcohol USP | 12.5 |
| Glycerin USP | 45.0 |
| Syrup USP | 20.0 |
| Flavoring Agent | qs |
| Purified Water qs ad | 100.0 |

Example 13

| Preparation of Oral Suspension (Syrup) | |
|---|---|
| Ingredient | % W/V |
| Active Compound as Aluminum Lake, Micronized | 0.05–5 (acid equivalent) |
| Polysorbate 80 USP | 0.1 |
| Magnesium Aluminum Silicate, Colloidal | 0.3 |
| Flavoring Agent | qs |
| Methyl Paraben USP | 0.18 |
| Propyl Paraben USP | 0.02 |
| Liquid Sugar | 75.0 |
| Purified Water qs ad | 100.0 |

Example 14

| Preparation of Injectable Solution | |
|---|---|
| Ingredient | % W/V |
| Active Compound | 0.05–5 |
| Benzyl Alcohol NF | 0.9 |
| Water for Injection | 100.0 |

Example 15

| Preparation of Injectable Oil | |
|---|---|
| Ingredient | % W/V |
| Active Compound | 0.05–5 |
| Benzyl Alcohol | 1.5 |
| Sesame Oil qs ad | 100.0 |

Example 16

| Preparation of Intra-Articular Product | |
|---|---|
| Ingredient | Amount |
| Active Compound | 2–20 mg |
| NaCl (physiological saline) | 0.9% |
| Benzyl Alcohol | 0.9% |
| Sodium Carboxymethylcellulose | 1–5% |
| pH adjusted to 5.0–7.5 | |
| Water for Injection qs to | 100% |

Example 17

| Preparation of Injectable Depo Suspension | |
|---|---|
| Ingredient | % W/V |
| Active Compound | 0.05–5 (acid equivalent) |
| Polysorbate 80 USP | 0.2 |
| Polyethylene Glycol 4000 USP | 3.0 |
| Sodium Chloride USP | 0.8 |
| Benzyl Alcohol NF | 0.9 |
| HCL to pH 6–8 | qs |
| Water for Injection qs ad | 100.0 |

The compounds of this invention may be administered internally, e.g., orally or parenterally, such as ntra-articularly, to a warm-blooded animal to inhibit complement in the body fluid of the animal, such inhibition being useful in the amelioration or prevention of those reactions dependent upon the function of complement, such as inflammatory process and cell membrane damage induced by antigen-antibody complexes. A range of doses may be employed depending on the mode of administration, the condition being treated and the particular compound being used. For example, for intravenous or subcutaneous use from about 5 to about 50 mg/kg/day, or every six hours for more rapidly excreted salts, may be used. For intra-articular use for large joints such as the knee, from about 2 to about 20 mg/joint per week may be used, with proportionally smaller doses for smaller joints. The dosage range is to be adjusted to provide optimum therapeutic response in the warm-blooded animal being treated. In general, the amount of compound administered can vary over a wide range to provide from about 5 mg/kg to about 100 mg/kg of body weight of animal per day. The usual daily dosage for a 70 kg subject may vary from about 350 mg to about 3.5 g. Unit doses can contain from about 0.5 mg to about 500 mg.

In therapeutic use the compounds of this invention may be administered in the form of conventional pharmaceutical compositions. Such compositions may be formulated so as to be suitable for oral or parenteral administration. The active ingredient may be combined in admixture with a pharmaceutically acceptable carrier, which carrier may take a wide variety of forms depending on the form of preparation desired for administration, i.e., oral or parenteral. The compounds can be used in compositions such as tablets. Here, the principal active ingredient is mixed with conventional tabletting ingredients such as corn starch, lactose, sucrose, sorbitol, talc, stearic acid, magnesium stearate, dicalcium phosphate, gums, or similar materials as non-toxic pharmaceutically acceptable diluents or carriers. The tablets or pills of the novel compositions can be laminated or otherwise compounded to provide a dosage form affording the advantage of prolonged or delayed action or predetermined successive action of the enclosed medication. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids or mixtures of polymeric acids with such materials as shellac, shellac and cetyl alcohol, cellulose acetate and the like. A particularly advantageous enteric coating comprises a styrene maleic acid copolymer together with known materials contributing to the enteric properties of the coating. The tablet or pill may be colored through the use of an appropriate non-toxic dye, so as to provide a pleasing appearance.

The liquid forms in which the novel compositions of the present invention may be incorporated for administration include suitable flavored emulsions with edible oils, such as, cottonseed oil, sesame oil, coconut oil, peanut oil, and the like, as well as elixirs and similar pharmaceutical vehicles. Sterile suspensions or solutions can be prepared for parenteral use. Isotonic preparations containing suitable preservatives are also desirable for injection use.

The term dosage form as described herein refers to physically discrete units suitable as unitary dosage for warm-blooded animal subjects, each unit containing a predetermined quantity of active component calculated to produce the desired therapeutic effect in association with the required pharmaceutical diluent, carrier or vehicle. The specification for the novel dosage forms of this invention are indicated by characteristics of the active component and the particular therapeutic effect to be achieved or the limitations inherent in the art of compounding such an active component for therapeutic use in warm-blooded animals as disclosed in this specification. Examples of suitable oral dosage forms in accord with this invention are tablets, capsules, pills, powder packets, granules, wafers, cachets, teaspoonfuls, dropperfuls, ampules, vials, segregated multiples of any of the foregoing and other forms as herein described.

The complement inhibiting activity of representative compounds of this invention has been demonstrated by one or more of the following identified tests: (i) Test, Code 026 (C1 inhibitor) This test measures the ability of activated human C1 to destroy fluid phase human C2 in the presence of C4 and appropriate dilutions of the test compound. An active inhibitor protects C2 from C1 and C4; (ii) Test, Code 035 (C3–C9 inhibitor) This test demonstrates the ability of the late components of human complement (C3–C9) to lyse EAC 142 in the presence of appropriate dilutions of the test compound. An active inhibitor protects EAC 142 from lysis by human C3–C9; (iii) Test, Code 036 (C-Shunt inhibitor) — In this test human erythrocytes rendered fragile are lysed in autologous serum via the shunt pathway activated by cobra venom factor in the presence of appropriate dilutions of the test compound. Inhibition of the shunt pathway results in failure of lysis; (iv) Forssman Vasculitis Test — Here, the well known complement dependent lesion, Forssman vasculitis, is produced in guinea pigs by intradermal injection of rabbit anti-Forssman antiserum. The lesion is measured in terms of diameter, edema and hemorrhage and the extent to which a combined index of these is inhibited by prior intraperitoneal injection of the test compound at 200 mg/kg is then reported, unless otherwise stated; (v) Forssman Shock Test — Lethal shock is produced in guinea pigs by an i.v. injection of anti-Forssman antiserum and the harmonic mean death time of treated guinea pigs is compared with that of simultaneous controls; (vi) Complement Level Reduction test In this test, the above dosed guinea pigs, or others, are bled for serum and the complement level is determined in undiluted serum by the capillary tube method of U.S. Pat. No. 3,876,376 and compared to undosed control guinea pigs; and (vii) Cap 50 Test — Here, appropriate amounts of the test compound are added to a pool of guinea pig serum in vitro, after which the undiluted serum capillary tube assay referred to above is run. The concentration of compound inhibiting 50% is reported.

Table I shows that representative compounds of the invention possess complement inhibitory activity.

TABLE I
BIOLOGICAL ACTIVITIES

| | ASSAY RESULTS | | | | |
| --- | --- | --- | --- | --- | --- |
| | IN VITRO | | | IN VIVO | |
| COMPOUND | 026* | 035 | 036 | FORSSMAN | % REDUCTION COMPLEMENT |
| 4-(m-Aminobenzamido)-5-hydroxy-1-naphthalenesulfonic acid sodium salt | 2** | NEG | 2 | — | — |
| 5-Hydroxy-4-{m-[3-(α,α,α-trifluoro-m-tolyl)-ureido]benzamido}-1-naphthalenesulfonic acid sodium salt | 1 (INT) | 2 (INT) | NEG (INT) | — | — |
| 4-{m-{3-[p-(Fluorosulfonoyl)phenyl]ureido}-benzamido}-5-hydroxy-1-naphthalenesulfonic acid sodium salt | NEG | NEG | NEG | 40 | −11 |
| 4,4'-[Ureylenebis(m-phenylenecarbonylimino)]bis[5-hydroxy-1-naphthalenesulfonic acid]disodium salt | 4 1 (INT) | 1 | 4 | 6 | 0 |
| 6-(m-Aminobenzamido)-4-hydroxy-2-naphthalenesulfonic acid sodium salt | NEG | 1 | NEG | −1 | +4 |
| 6,6'-[Ureylenebis(m-phenylenecarbonylimino)]-bis[4-hydroxy-2-naphthalenesulfonic acid] disodium salt | NEG | 1 | NEG | −1 | +4 |

*Tests identified by code herein
**Numbers represent activity in wells, a serial dilution assay, higher well number indicates higher activity.
INT = Interfering with assay, but not necessarily inactive.

We claim:

1. A method of inhibiting the complement system in a warm-blooded animal which comprises internally administering to said animal an effective complement inhibiting amount of a compound selected from those of the formula:

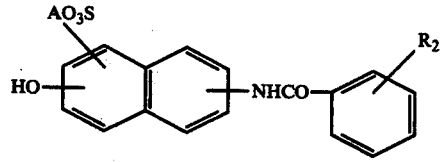

wherein R₂ is

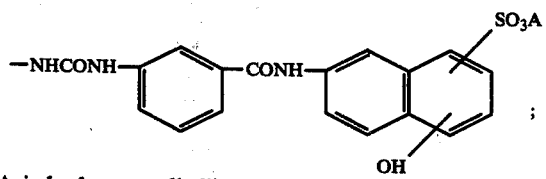

A is hydrogen, alkali metal or alkaline earth, with the proviso that each A is identical in the same compound.

2. A method according to claim 1 wherein the compound is 6,6'-[ureylenebis(m-phenylenecarbonylimino)] bis-[4-hydroxy-2-naphthalenesulfonic acid] disodium salt.

* * * * *

UNITED STATES PATENT OFFICE
CERTIFICATE OF CORRECTION

Patent No. 4,131,684          Dated December 26, 1978

Inventor(s) Seymour Bernstein

It is certified that error appears in the above-identified patent and that said Letters Patent are hereby corrected as shown below:

Section [75] Inventors, delete "Milton D. Heller of New City, N.Y.".

Signed and Sealed this

Tenth Day of April 1979

[SEAL]

Attest:

RUTH C. MASON
Attesting Officer

DONALD W. BANNER
Commissioner of Patents and Trademarks